(12) United States Patent
Levin et al.

(10) Patent No.: US 6,358,198 B1
(45) Date of Patent: Mar. 19, 2002

(54) LAPAROSCOPIC/THORASCOPIC SUPPORT DEVICE

(76) Inventors: John M. Levin; Matthew Wallash Levin, both of 412 Fairview Ave., Narberth, PA (US) 19072

( * ) Notice: Subject to any disclaimer, the term of this patent is extended or adjusted under 35 U.S.C. 154(b) by 0 days.

(21) Appl. No.: 09/571,236

(22) Filed: May 16, 2000

Related U.S. Application Data (60) Provisional application No. 60/134,639, filed on May 18, 1999.

(51) Int. Cl.$^7$ ............................................. A61F 2/00
(52) U.S. Cl. ........................................................ 600/37
(58) Field of Search ................................ 600/204, 208, 600/37

(56) References Cited

U.S. PATENT DOCUMENTS

| | | | | |
|---|---|---|---|---|
| 5,215,521 A | * | 6/1993 | Cochran et al. | 600/37 X |
| 5,279,539 A | * | 1/1994 | Bohan et al. | 600/37 |
| 5,337,736 A | * | 8/1994 | Reddy | 600/37 X |
| 5,337,754 A | * | 8/1994 | Heaven et al. | 600/37 X |
| 5,362,294 A | * | 11/1994 | Seitzinger | 600/37 |
| 5,919,233 A | * | 7/1999 | Knpf et al. | 600/37 X |
| 6,261,222 B1 | * | 7/2001 | Schweich, Jr. et al. | 600/16 |
| 6,264,604 B1 | * | 7/2001 | Kieturakis et al. | 600/207 |
| 6,273,852 B1 | * | 8/2001 | Lehe et al. | 600/30 |
| 6,277,136 B1 | * | 8/2001 | Bonutti | 606/190 |
| 6,283,940 B1 | * | 9/2001 | Mulholland | 604/96.01 |

FOREIGN PATENT DOCUMENTS

| WO | WO 00/24320 | * | 5/2000 | ................ 606/116 |
|---|---|---|---|---|

* cited by examiner

Primary Examiner—John P. Lacyk
Assistant Examiner—Joseph A Cadugan
(74) Attorney, Agent, or Firm—Caesar, Rivise, Bernstein, Cohen & Pokotilow, Ltd.

(57) ABSTRACT

A laparoscopic/thorascopic support device is described that engages and supports a body part in a non-traumatic manner while it is being acted upon by a surgical instrument. The support device is capable of lifting or otherwise moving a body part into a desired position to be operated upon or isolated from another body part. The support device includes an insertion device that punctures a covering of a body tissue to provide a passageway for access to the desired body part and a catheter. The catheter extends through the passageway and engages and temporarily supports the desired body part in a non-traumatic manner. The catheter (or manipulating device) includes a shaft made of a material that is sufficiently flexible to bend to a desired straight or curved orientation and is sufficiently rigid to maintain the desired orientation. According to the preferred embodiments of the invention, a distal end of the shaft bends about the desired body part to form a loop and secure the desired part within the loop. Preferably, the catheter also includes an eyelet on the shaft that retains the distal end of the shaft, and a first balloon located at the distal end that is directed through a central passage of the eyelet and is expanded to lock the catheter about the desired body part. A second balloon may be placed at the distal end of the shaft spaced apart from and inside the first balloon and expanded at an opposite side of the eyelet from the first balloon to prevent the catheter from cinching down and traumatizing the desired body part. Alternatively, the shaft may include a distal end having a curved configuration that is made of a material having sufficient elastic memory that can be straightened for insertion into the passageway or placement about the desired body part, and resumes its curved configuration due to its elastic memory to at least partially encircle and support the desired body part.

18 Claims, 6 Drawing Sheets

LAPAROSCOPIC/THORASCOPIC SUPPORT DEVICE

SPECIFICATION

This application claims the benefit of the filing date of U.S. Provisional Application Ser. No. 60/134,639, filed on May 18, 1999, entitled Laparoscopic/Thorascopic Support Device, which was filed by the same inventors as this invention, and whose disclosure is incorporated by reference herein.

FIELD OF THE INVENTION

This invention relates to generally to surgical instruments, and more specifically, to laparoscopic and thorascopic instruments that engage and support a body part.

BACKGROUND OF THE INVENTION

In laparoscopic and thorascopic surgical procedures, it is often necessary to engage and/or support a body part, especially of tubular shape (e.g., bowel, fallopian tube, esophagus, appendix, etc.) to be worked upon by, or isolated from, a surgical device (e.g., dissector, scissors, biopsy instrument, etc.). Morever, during these and other surgical procedures, it is quite common to employ a clamp or other gripping device to immobilize or engage a body part to be acted upon or isolated from, a laparoscopic/thorascopic surgical instrument which may cause undesired trauma to that body part. Unfortunately, the related art does not show an effective laparoscopic or thorascopic tool that would allow a surgeon to manipulate a body part without causing undesired trauma to that body part. Accordingly, a need exists for a laparoscopic/thorascopic support device that supports the body part in a non-traumatic manner while it is being acted upon by or isolated from a laparoscopic/thorascopic surgical instrument.

References throughout this application to "laparoscopic," in referring either to a surgical procedure or a surgical device, or instrument, is intended to include within its scope thorascopic procedures, devices or instruments, unless the context of the reference to laparoscopic clearly indicates otherwise.

SUMMARY OF THE INVENTION

Accordingly, it is an object of the invention to substantially obviate one or more of the problems associated with the related art.

It is also an object of the invention to provide a laparoscopic/thorascopic support device.

It is another object of the invention to provide a support device that moves or supports a body part in a non-traumatic manner.

It is yet another object of the invention to obviate the need for one or more airlock standard trocars, especially in more complex procedures during which extra trocars and retractors are routinely required.

It is also an object of the invention to provide a support device that is capable of lifting or otherwise moving a body part to a desired position.

The objects of the invention can be achieved, as a whole or in part, by a support device for engaging and temporarily supporting a desired body part of the patient's body comprising an insertion device and a catheter or manipulating device. The insertion device punctures a covering of a body tissue to provide a passageway for access to the desired body part. The catheter (or manipulator) extends through the passageway, engages and temporarily supports a desired body part in a non-traumatic manner, and includes a shaft made of a material that is sufficiently flexible to bend to a desired straight or curved orientation and is sufficiently rigid to maintain the desired orientation. A distal end of the shaft bends about the desired body part to form a loop and secure the desired body part within the loop.

In a preferred embodiment of the invention, the catheter also includes an eyelet on a central region of the shaft for retaining the distal end of the shaft to form a closed loop, and a first balloon at the distal end that is directed through a central passage of the eyelet and is expanded to lock the catheter about the desired body part. The catheter can also include a second balloon at the distal end spaced apart from and inside the first balloon that is expanded at an opposite side of the eyelet from the first balloon to prevent the shaft of the catheter from cinching down and traumatizing the desired body part.

In another preferred embodiment of the invention, the shaft includes a distal end having a curved configuration that is made of a material having sufficient elastic memory that can be straightened for insertion into the passageway or placement about the desired body part, and that resumes its curved configuration due to its elastic memory to at least partially encircle and support the desired body part.

The objects of the invention can also be achieved, as a whole, or in part, by a method for engaging and temporarily supporting a desired body part of a patient's body comprising puncturing a covering of a body tissue to provide a passageway for insertion of a catheter into an area of the desired body part, inserting a shaft of the catheter into the passageway, engaging the body part by directing a distal end of the shaft about the desired body part to form a loop, and securing the desired body part within the loop.

The objects of the invention can also be achieved, as a whole or in part, by a support system for engaging and temporarily supporting a desired body part of a patient's body, comprising an elongated hollow needle, a catheter, and a grasping device. The elongated hollow needle includes a distal sharp end that punctures and penetrates a covering of a body tissue, with the needle defining a cylindrical compartment that provides the passageway for access to the desired body part. The catheter extends through the passageway to engage the body part. The catheter includes a shaft made of a material that is sufficiently flexible to bend to a desired straight or curved orientation and is sufficiently rigid to maintain the desired orientation. The grasping device directs a distal end of the shaft about the desired body part to form a loop for securing the desired body part.

BRIEF DESCRIPTION OF THE DRAWINGS

The invention will be described in conjunction with the following drawings in which like referenced numerals designate like elements, and wherein.

DETAILED DESCRIPTION OF THE INVENTION

The present invention relates to a unique laparoscopic/thorascopic support device that engages and supports a body part in a non-traumatic manner while it is being acted upon by a laparoscopic/thorascopic surgical instrument. The laparoscopic/thorascopic support device of the invention is capable of lifting or otherwise moving a body part into a desired position to be operated upon or isolated from a surgical site.

Referring to FIGS. 1–5, a support device 10 of a preferred embodiment of this invention includes an elongate, balloon catheter 12 that is connectable to a syringe (not shown) at a proximal end thereof, in a conventional manner. Preferably, the catheter 12 is sufficiently rigid to retain a desired orientation as it is being manipulated within the abdomen of a patient to move under, or partially about a body part to be supported. Accordingly, the catheter may be formed of plastic and resilient metals, such as titanium.

In the illustrated embodiment of FIGS. 1–5, the catheter 12 is a double lumen member including two balloons 14, 16 spaced apart from each other at a distal end. Spaced proximally of the balloons and attached to the outer wall of the catheter body is a loop or eyelet 18 including a central passage 20 for receiving the distal end 22 of the catheter, in a manner which will be explained hereinafter.

It should be understood that in accordance with the broadest aspects of this invention, the catheter can be of a single lumen type, and can employ a single balloon (e.g., 14) at the distal end thereof. However, in the most preferred embodiments of the invention, a double lumen catheter is employed with two balloons 14 and 16, for purposes that will become apparent by the discussion that follows.

The balloons 14 and 16 are normally in a collapsed condition, until filled with a fluid injected into the catheter from a syringe at the proximal end thereof, in a conventional manner. Most preferably the balloons are relatively stiff; similar to balloons employed in balloon angioplasty procedures in human arteries.

The manner of employing the laparoscopic/thorascopic support device 10 of this invention will now be described.

Figure 1:
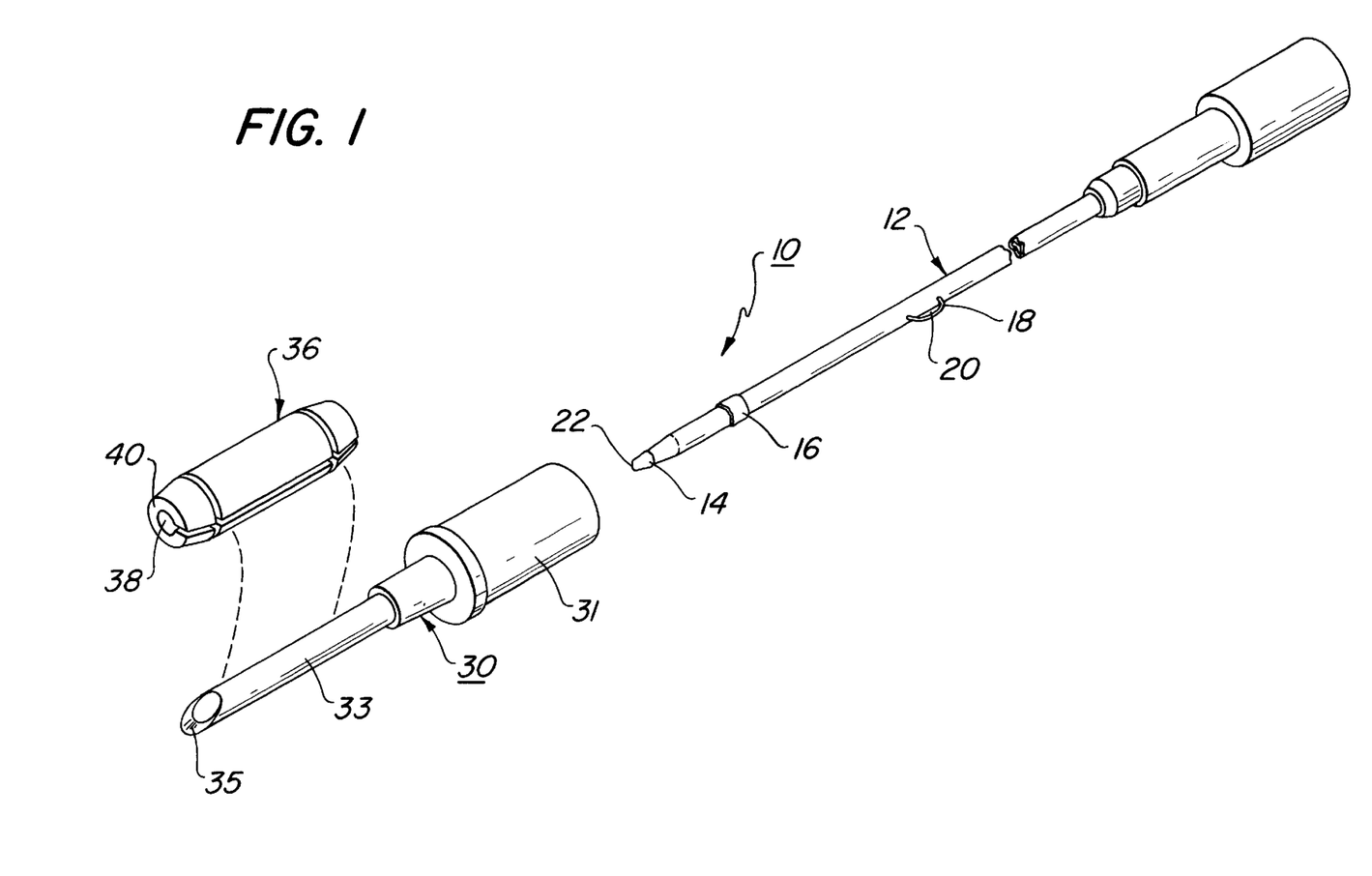
FIG. 1 is an exploded isometric view showing a support device in accordance with a preferred embodiment of the invention.
Figure 2:
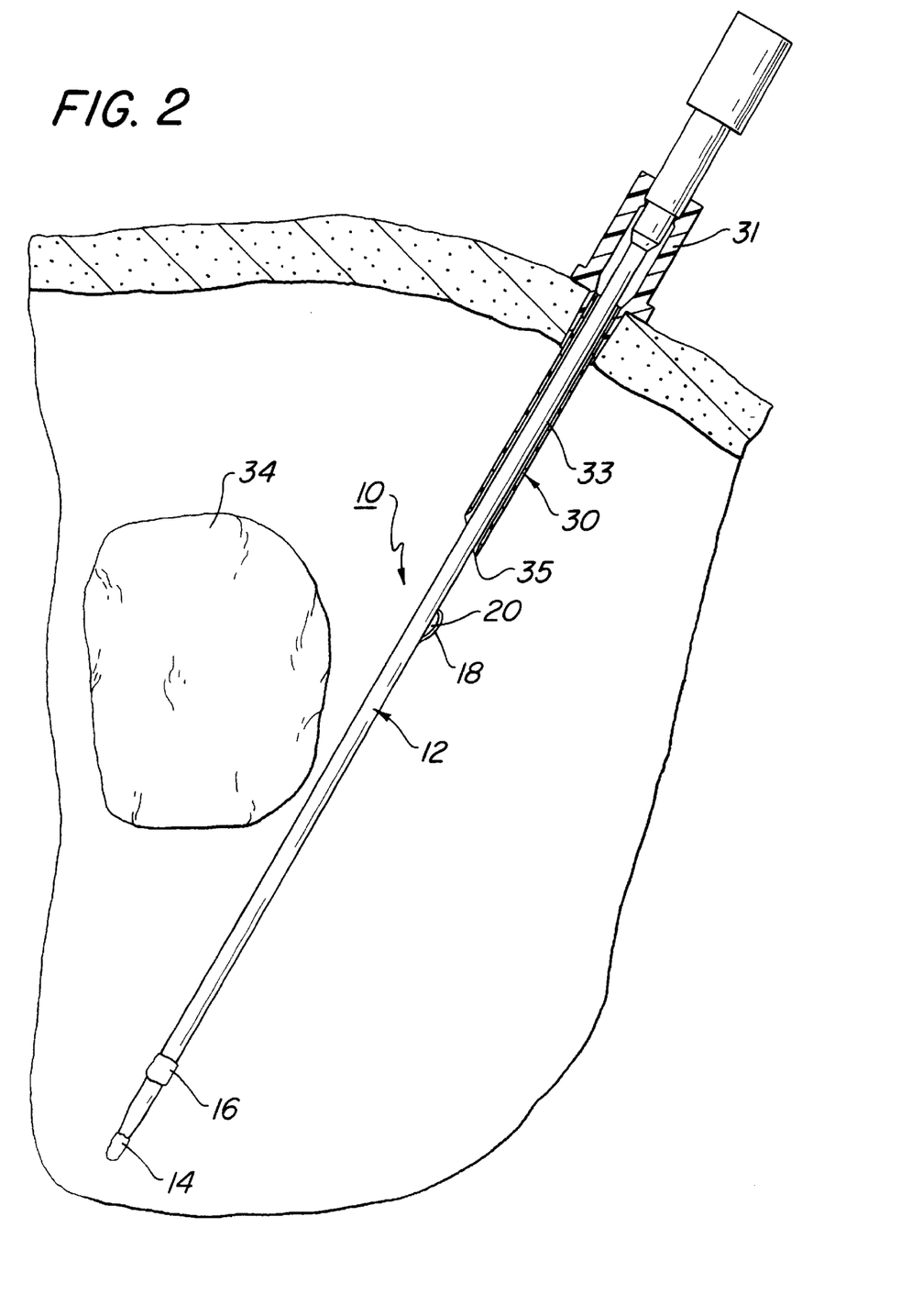
FIG. 2 is a sectional view illustrating the support device of FIG. 1 extending into a body cavity.
Figure 3:
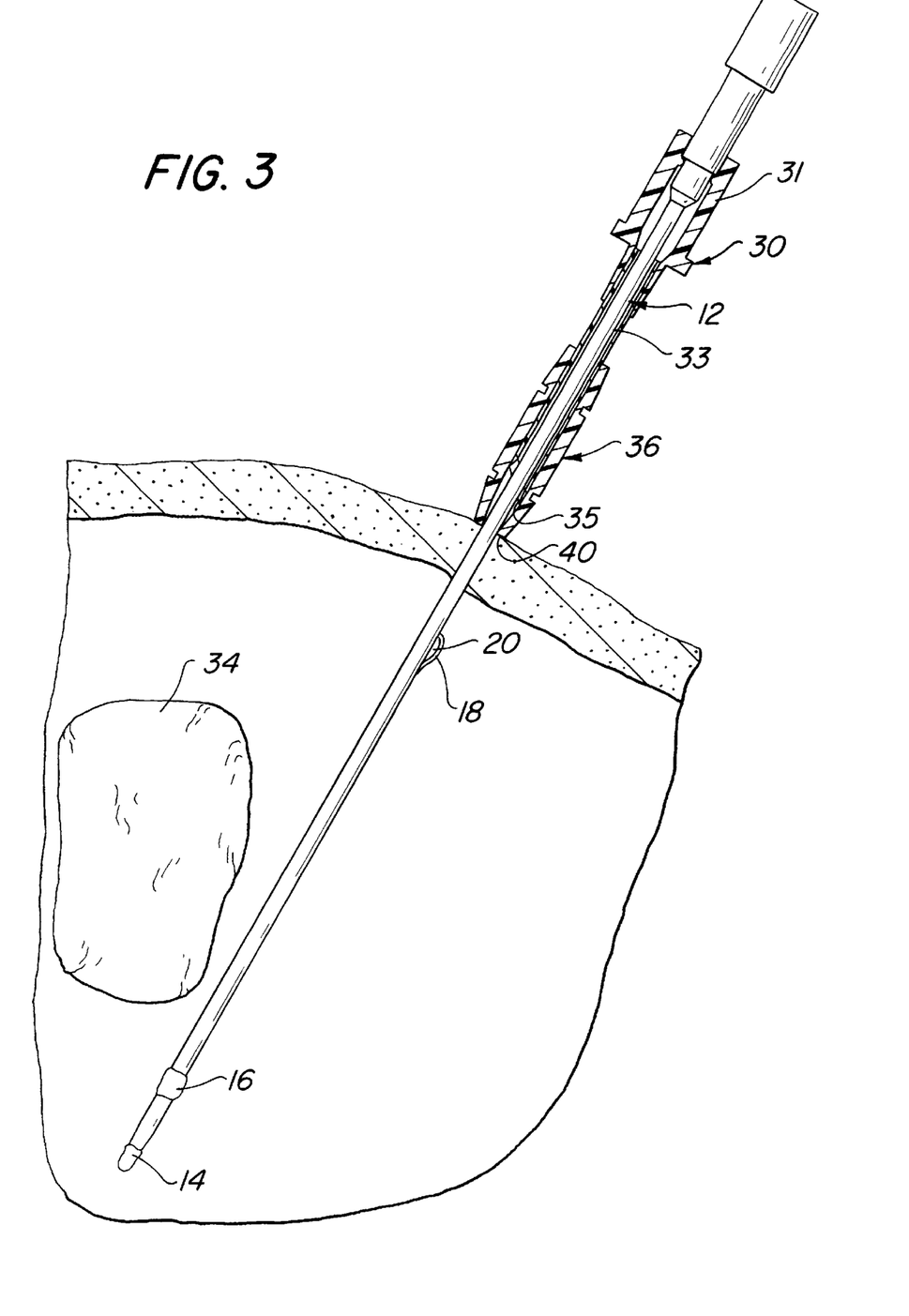
FIG. 3 is a sectional view of the supporting device of FIGS. 1 and 2 after the insertion device has been retracted from an abdomen wall.

Referring to FIGS. 1 and 2, an insertion device 30 includes an upper cap member 31 and a lower, or distal, needle 33. The needle 33 has a width of, for example, about 14 gauge, and is employed to puncture the abdomen 32 of a patient, and thereby provide a passageway for the catheter 12 to be inserted into an area of the body near the body part 34 to be acted upon. After the catheter 12 has been inserted through the insertion device 30 into the abdomen, as is shown in FIG. 2, the insertion device is retracted, as shown in FIG. 3, to move the distal sharp edge 35 of the needle 33 into a region outside of the patient's body. Thereafter, a clip 36, in the form of a split sleeve defining a cylindrical compartment 38 therethrough is inserted about the distal end of the needle 33 of the insertion device 30, and about an adjacent section of the catheter 12. This clip 36 is of a well-known construction, and is employed to prevent the distal needle 33 of the device 30 from canting, or rotating, relative to the catheter 12 and thereby cutting the catheter 12 during a surgical procedure.

Figure 4:
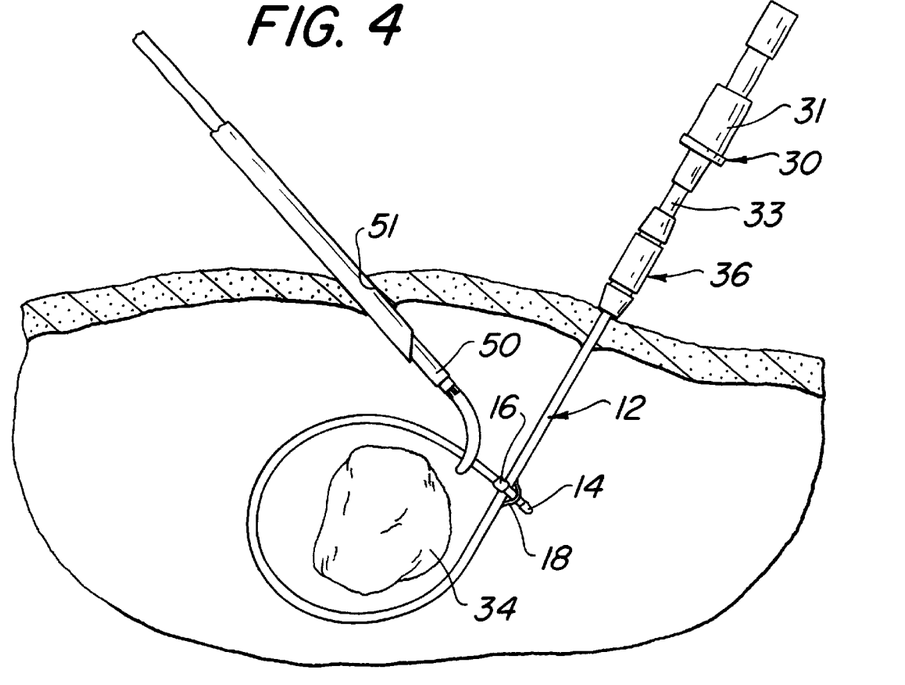
FIG. 4 is a sectional view illustrating the supporting device of FIG. 3 with a shaft forming a loop.
Figure 5:
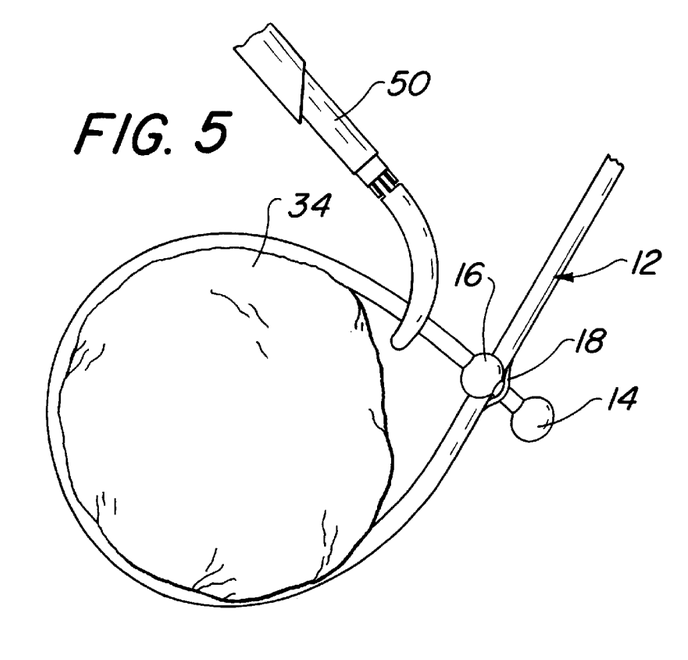
FIG. 5 is an enlarged view illustrating the supporting device of FIG. 4 gripping, or supporting, an internal body part.

Moreover, in a preferred form of the invention as shown in FIGS. 3 and 4, the clip 36 also functions as a keeper, with the lower, or distal surface 40 thereof engaging the outer surface of the abdomen and thereby maintaining the catheter 12 in a desired orientation and position within the patient's body. Thus, prior to applying the clip 36 to the needle 33 and the catheter 12, it is important that the catheter 12 be properly located in the operating site.

Referring to FIG. 4, after positioning the catheter 12 within the abdomen, a laparoscopic grasping device 50 of any suitable design is inserted through a trocar or other passage 51 in a different area of the abdomen from the insertion device 30 and the catheter 12, and then is directed into the operating site near the body part 34 to be acted upon, to grip a region of the catheter 12 adjacent the distal end thereof, (See FIGS. 4 and 5) and manipulate that region about the body part 34 to be supported. The distal region of the catheter 12 is then directed through the central passage 20 of the loop or eyelet 18; preferably with the collapsed balloons 14 and 16 being located on opposed sides of the eyelet 18. Thereafter, a syringe (not shown) connected to the proximal end of the catheter 12 in a well-known manner is operated to direct fluid into both inner and outer lumens of the catheter 12 to thereby expand the balloons 14 and 16 on opposite sides of the eyelet 18, as is shown most clearly in FIG. 5. The catheter 12 supports the body part 34 in a non-traumatic fashion, and the engagement of the balloons 14 and 16 on opposite sides of the eyelet 18 retains the catheter 12 about the body part 34 and prevents the catheter 12 from cinching down and crimping, or otherwise traumatizing, the body part 34. In this condition, the catheter 12 can then be manipulated to position the body part 34 in a desired orientated relative to the operating instruments and the surgical field to permit a laparoscopic surgical procedure to be carried out in an efficient, safe manner.

As explained earlier, in accordance with the broadest aspects of this invention, a single balloon can be employed in lieu of the double lumen-double balloon arrangement described above. In this case, the single balloon 14 will be positioned through the eyelet 18 and then expanded by fluid directed into the balloon 14 from the syringe to thereby lock the catheter 12 about a desired body part. However, in accordance with this embodiment of the invention it may be possible for the catheter 12 to actually cinch down and undesirably crimp the body part 34. Therefore, for surgical procedures in which there is a significant concern regarding the possibility of crushing the body part to be acted upon, the double lumen-double balloon arrangement described earlier is preferred.

It also should be noted that, if desired, a separate disc-shaped keeper member (not shown) can be disposed solely about the catheter 12 in a region below the clip 36, to provide the function of maintaining the catheter 12 in a proper position within the operating site.

Referring to FIGS. 6–9, an alternative embodiment of the invention in the form of a support device/retractor is illustrated at 100. The support device/retractor 100 is directed into the operating site through an insertion device 102, which can be the same as insertion device 30. In particular, the insertion device 102 includes an upper cap member 104 and a lower, or distal hollow needle 106. This insertion device 102, like the device 30, is employed to percutaneously puncture a patient's skin, to thereby provide an entry passageway for the support device/retractor 100 of this invention.

Figures 6, 7:
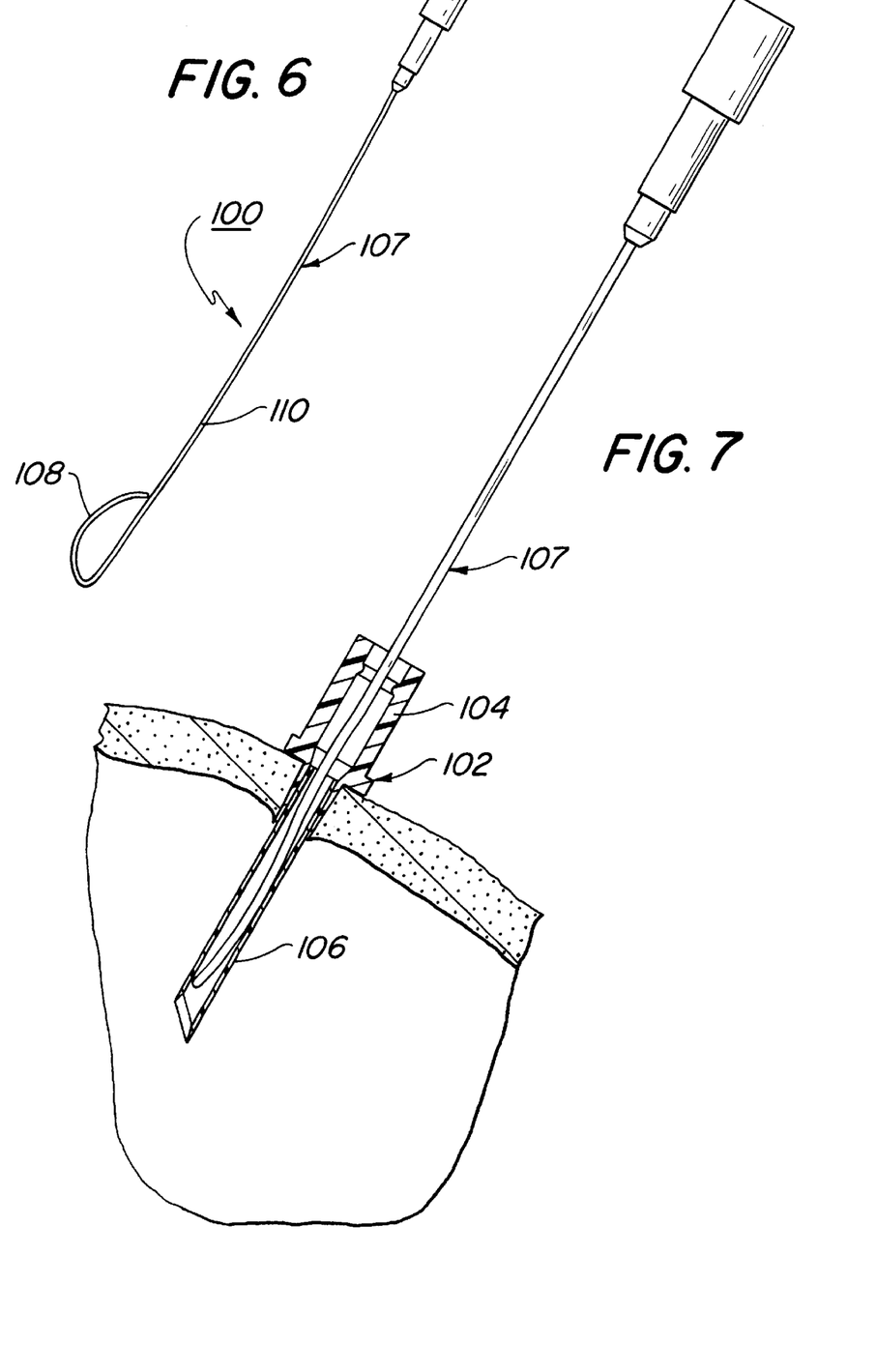
FIG. 6 is an elevational view illustrating a catheter in accordance with another preferred embodiment of the invention.
FIG. 7 is an enlarged sectional view of the catheter shown in FIG. 6 and an insertion device that together form a supporting device in accordance with yet another preferred embodiment of the invention.

In this later embodiment of the invention, and as is shown in FIG. 6, the support device/retractor 100 initially is formed with a shaft 107 having a curved distal end 108 that is sufficiently rigid to maintain its curvature during use, but is sufficiently springy to be manually moved into a substantially linear or straight condition generally aligned with elongate section 110 of the shaft 107 as shown within the hollow needle 106 of the insertion device 102. (See FIG. 7) The shaft 107 of the support device/retractor 100 is made of a material having sufficient elastic memory for its initially formed condition so that the distal end 108 automatically will return to its curved configuration illustrated in FIG. 6, after an instrument employed to straighten the distal end 108 has been removed.

In view of the above construction, the curved distal end 108 of the support device/retractor 100 initially is straightened so that it can be directed through the central passage of the insertion device 102, and after passage therethrough, the distal end 108 reassumes its curved configuration due to its elastic memory for that orientation. In this embodiment of the invention, the insertion device 102 can be partially retracted, and the clip 36 employed, in the same manner as described above in connection with the support device 10 (e.g., see FIG. 9).

Figure 8:
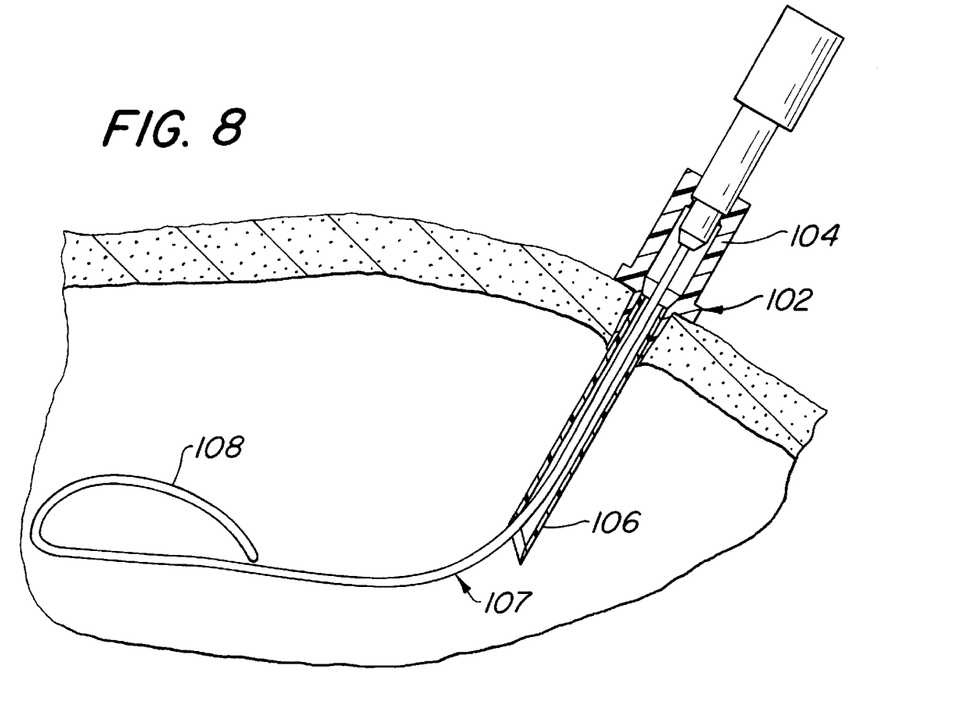
FIG. 8 is a sectional view illustrating the supporting device shown in FIG. 7.

In one use of the support device, the curved distal end 108, as shown in FIG. 8, can be employed as a conventional retractor to push against tissue or organs that are obstructing a surgical site/procedure. For example, during gallbladder surgery, it is common for the caudate lobe of the liver to move into the surgical field; thereby requiring its retraction. The support device/retractor 100 of this invention can be employed for this latter purpose. Obviously, the support device/retractor 100 of this invention can be employed in a number of other surgical environments where other organs or tissue need to be removed from the surgical site.

Figure 9:
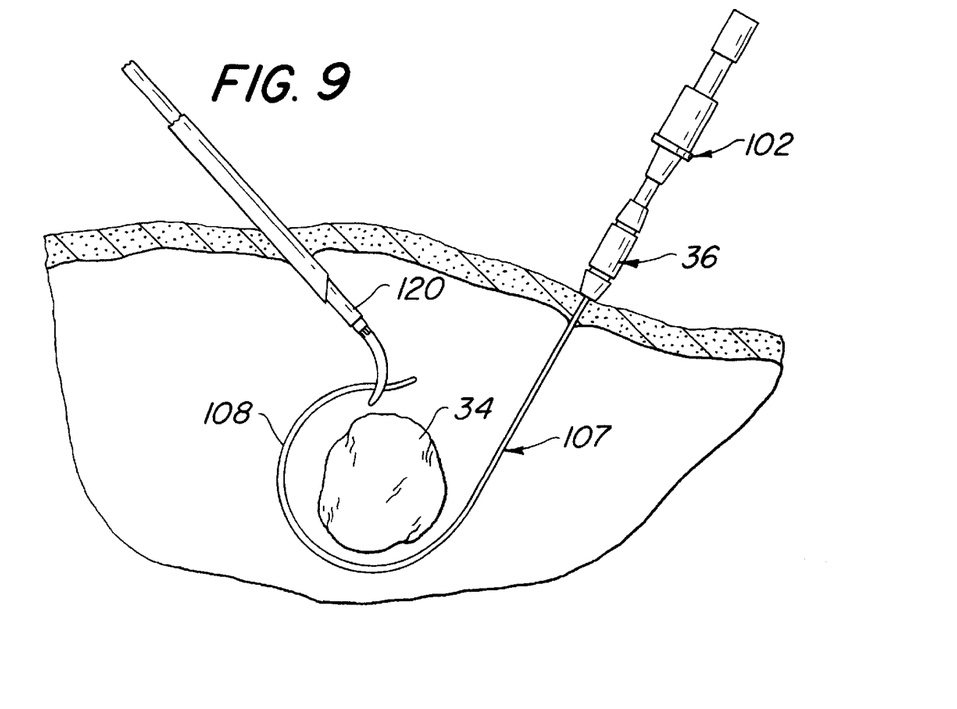
FIG. 9 is a sectional view illustrating the supporting device of FIGS. 7 and 8, but being manipulated about a body part.

In an alternative manner of using the support device/ retractor 100, as shown in FIG. 9, a separate, manipulating instrument 120 can be employed to open up the curved distal end 108 while it is in the surgical field, and then direct the open end about the organ or body part 34 to be supported by the support device/retractor 100 in a manner similar to that described earlier in connection with the support device of the first embodiment of the invention. Thereafter, the manipulating instrument 120 is removed from the support device/retractor 100, thereby permitting the distal end 108 of the support device/retractor 100 to move toward its originally formed, curved configuration due to its elastic memory, to thereby at least partially encircle and support the organ 34 or other tissue to be acted upon and/or removed from the surgical site. (FIG. 9)

It should be understood that the shaft 107 of the support device/retractor 100 can be formed from any suitable material that is compatible with body tissues; that is capable of being formed into a shaped configuration; that has an elastic memory for its initially formed configuration and that is capable of being straightened or otherwise reoriented to a second position for permitting the support device/retractor 100 to be directed into a patient's body through an insertion device 102, while still retaining the elastic memory of the shaft 107 for its initially formed, unstraightened configuration.

In particular, the support device/retractor 100 includes a shaft 107 that can be straightened to be received within the insertion device 102, and the shaft 107 includes an elastic memory for its initially formed, curved configuration. Suitable materials usable to form the shaft 107 of the support device/retractor 100 include plastic materials which can be elastically oriented and set so as to retain memory for its deformed configuration, and also certain metals, such as titanium. Materials having an elastic memory for an initially formed configuration, while being physically movable into a straight or other configuration, are well known to persons skilled in the art; the specific material employed not constituting a limitation on the broadest aspects of this invention.

It should be apparent from the aforementioned description and attached drawings that the concept of the present application may be readily applied to a variety of preferred embodiments, including those disclosed herein. Without further elaboration, the foregoing will also fully illustrate the invention that others may, by applying current or future knowledge, readily adapt the same for use under various conditions of service.

We claim:

1. A support device for engaging and temporarily supporting a desired body part of a patient's body in a non-traumatic manner, comprising:
   an insertion device adapted to puncture a covering of a body tissue to provide a passageway to the desired body part; and
   a catheter adapted to extend through the passageway, engage and temporarily support the desired body part in a non-traumatic manner, said catheter including a shaft made of a material that is sufficiently flexible to bend to a desired straight or curved orientation and is sufficiently rigid to maintain the desired orientation,
   wherein a distal end of said shaft is adapted to bend about the desired body part to form a loop and secure the desired body part within the loop,
   wherein said shaft of said catheter includes an eyelet for retaining said distal end of said shaft to form a closed loop, and a first balloon at said distal end that is directed through a central passage of said eyelet, wherein said first balloon is adapted to be expanded to lock said catheter about the desired body part.

2. The support device of claim 1, wherein said catheter further includes a second balloon at said distal end spaced proximally from said first balloon that is adapted to expand at an opposite side of said eyelet from said first balloon to prevent said catheter from cinching down and traumatizing the desired body part.

3. The support device of claim 2, wherein said first balloon is in a compressed state for passage through said eyelet.

4. The support device of claim 1, wherein said shaft includes a distal end having a curved configuration that is made of a material having sufficient elastic memory to be straightened for insertion into the passageway or placement about the desired body part and then reassume its curved configuration to at least partially encircle and support the desired body part.

5. The support device of claim 1, wherein said insertion device comprises an elongated hollow needle having a distal sharp end adapted to puncture and penetrate the covering of the body tissue, said needle defining a cylindrical compartment that provides a passageway for insertion of said catheter through the covering.

6. The support device of claim 5, wherein said insertion device further comprises a cap member located at a remote end of said insertion device opposite said sharp end and having a radius larger than a radius of said needle for stopping penetration of said insertion device when said cap member abuts the outer surface of the covering of the body tissue, said cap member defining a cylindrical compartment therethrough and extending to said cylindrical compartment of said needle for receiving said catheter.

7. The support device of claim 5, further comprising a sleeve defining a cylindrical compartment therethrough for insertion about said distal sharp end of said hollow needle and about a section of said catheter adjacent to said distal sharp end for preventing said insertion device from canting or rotating relative to said catheter.

8. The support device of claim 7, wherein said sleeve engages the outer surface of the covering to maintain said catheter in a desired orientation and position within the patient's body.

9. The support device of claim 1, further comprising a disk-shaped keeper disposed around said catheter that engages the outer surface of the covering to maintain said catheter in a desired orientation and position within the patient's body.

10. The support device of claim 1, wherein the covering is an abdomen wall.

11. The support device of claim 1, wherein the covering is skin.

12. A method for engaging and temporarily supporting a desired body part of a patient's body in a non-traumatic manner, comprising:

(a) puncturing a covering of a body tissue with a sharp end of an insertion device to provide a passageway for insertion of a catheter through the covering and into an area of the desired body part;

(b) inserting a shaft of the catheter into the passageway;

(c) engaging the body part in a non-traumatic manner by directing a distal end of the shaft about the desired body part to form a loop;

(d) inserting the distal end of the shaft through an eyelet, said eyelet being formed along the shaft and spaced proximally from the distal end, to close the loop; and (e) expanding a first balloon located at the distal end to prevent the distal end from retracting back through the eyelet.

13. The method of claim 12, further comprising: (f) expanding a second balloon, located at the distal end spaced apart from and inside the first balloon, at an opposite side of the eyelet from the first balloon to prevent the catheter from cinching down and traumatizing the desired body part.

14. The method of claim 12, wherein the distal end has a curved configuration that is made of a material having sufficient elastic memory to reassumes its curved configuration upon the removal of an external bias, and the method further comprises straightening the distal end for insertion into the passageway or for placement about the desired body part to at least partially encircle and support the desired body part.

15. The method of claim 12, further comprising:

retracting the insertion device to a region outside the covering; and inserting a clip about the sharp end of the insertion device and an adjacent section of the catheter to prevent the insertion device from canting or rotating relative to the catheter.

16. A support system for engaging and temporarily supporting a desired body part of a patient's body in a non-traumatic manner, comprising:

an elongated hollow needle having a distal sharp end adapted to puncture and penetrate a covering of a body tissue, said needle defining a cylindrical compartment that provides the passageway for access to the desired body part;

a catheter adapted to extend through the passageway and engage the body part in a non-traumatic manner, said catheter including a shaft made of a material that is sufficiently flexible to bend to a desired straight or curved orientation and is sufficiently rigid to maintain the desired orientation;

a grasping device for directing a distal end of said shaft about the desired body part to form a loop for securing the desired body part;

an eyelet on said shaft of said catheter for retaining said distal end of said shaft; and a first balloon at said distal end that is directed through a central passage of said eyelet, wherein said first balloon is adapted to be expanded to lock said catheter about the desired body part.

17. The support system of claim 16, wherein said catheter further comprises:

a second balloon at said distal end of said shaft spaced proximally from said first balloon, said second balloon being adapted to expand at an opposite side of said eyelet from said first balloon to prevent said catheter from cinching down and traumatizing the desired body part.

18. The support system of claim 16, wherein said shaft includes a distal end having a curved configuration that is made of a material having sufficient elastic memory to be straightened for insertion into the passageway or placement about the desired body part and then reassume its curved configuration to at least partially encircle and support the desired body part.

* * * * *